(12) United States Patent
Kozlowski et al.

(10) Patent No.: US 8,461,295 B2
(45) Date of Patent: *Jun. 11, 2013

(54) METHODS FOR PREPARING POLYMERIC REAGENTS AND COMPOSITIONS OF POLYMERIC REAGENTS

(75) Inventors: Antoni Kozlowski, Huntsville, AL (US); Jon McKannan, Huntsville, AL (US); Samuel P. McManus, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,686

(22) Filed: May 3, 2012

(65) Prior Publication Data
US 2012/0214952 A1    Aug. 23, 2012

Related U.S. Application Data

(63) Continuation of application No. 12/820,124, filed on Jun. 21, 2010, now Pat. No. 8,193,306, which is a continuation of application No. 11/497,463, filed on Jul. 31, 2006, now Pat. No. 7,767,784.

(60) Provisional application No. 60/703,709, filed on Jul. 29, 2005.

(51) Int. Cl.
*C08G 73/00*  (2006.01)
*C08G 65/00*  (2006.01)
*C08G 65/34*  (2006.01)

(52) U.S. Cl.
USPC ........... 528/422; 528/423; 528/425; 528/272; 528/481; 528/486; 528/502 R; 528/503

(58) Field of Classification Search
USPC ................. 528/422, 423, 425, 272, 481, 486, 528/502 R, 503
See application file for complete search history.

(56) References Cited

U.S. PATENT DOCUMENTS

| 5,281,698 | A | 1/1994 | Nitecki |
| 5,629,384 | A | 5/1997 | Veronese et al. |
| 5,922,675 | A | 7/1999 | Baker et al. |
| 5,932,462 | A | 8/1999 | Harris et al. |
| 6,348,558 | B1 | 2/2002 | Harris et al. |
| 6,362,254 | B2 | 3/2002 | Harris et al. |
| 6,624,246 | B2 | 9/2003 | Kozlowski |
| 7,608,253 | B2 | 10/2009 | Bentley et al. |
| 7,767,784 | B2 | 8/2010 | Kozlowski et al. |
| 8,193,306 | B2 * | 6/2012 | Kozlowski et al. ............ 528/422 |
| 2008/0064851 | A1 | 3/2008 | Kozlowski et al. |
| 2010/0256310 | A1 | 10/2010 | Kozlowski et al. |

FOREIGN PATENT DOCUMENTS

| WO | WO 01/45796 | 6/2001 |
| WO | WO 2004/047871 | 6/2004 |

OTHER PUBLICATIONS

Harris, et al., "Effect of PEGylation on Pharmaceuticals", Nat. Rev. Drug Discovery, vol. 2, pp. 214-221, (2003).
Ouchi, et al., "Design of Antitumor Agent-Terminated Poly(Ethylene Glycol) Conjugate as Macromolecular Prodrug", Polymer Preprints, pp. 582-583, (1997).
Ouchi, et al., "Synthesis and Antitumor Activity of Poly(Ethylene Glycol)s Linked to 5-Fluorouracil via a Urethane or Urea Bond", Drug Design and Discovery, vol. 9, pp. 93-105, (1992).
Sims, et al., "A Method for the Estimation of Polyethylene Glycol in Plasma Protein Fractions", Analytical Biochemistry, vol. 107, pp. 60-63, (1980).
Zalipsky, "Synthesis of an End-Group Functionalized Polyethylene Glycol-Lipid Conjugate for Preparation of Polymer-Grafted Liposomes", Bioconjugate Chem., vol. 4, pp. 296-299, (1993).
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
POLYPURE Products, PEG amines; PEG acids and amino acids; PEG thiols and disulfides; Biotins, 5 pages, (Apr. 2004).
POLYPURE Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).

(Continued)

*Primary Examiner* — Duc Truong
(74) *Attorney, Agent, or Firm* — Mark A. Wilson

(57) ABSTRACT

Methods for preparing active carbonate esters of water-soluble polymers are provided. Also provided are other methods related to the active carbonate esters of water-soluble polymers, as well as corresponding compositions.

4 Claims, No Drawings

OTHER PUBLICATIONS

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

PCT International Search Report corresponding to PCT Application No. PCT/US2006/029929 date of mailing Jan. 19, 2007.

PCT International Preliminary Report on Patentability corresponding to PCT Application No. PCT/US2006/029929 date of mailing Feb. 7, 2008.

Office Communication dated Feb. 22, 2011, corresponding to Australian Patent Application No. 2006275473.

Chinese First Office Action corresponding to Chinese Patent Application No. 200680030236.3 date of notification Jun. 11, 2010.

European Communication corresponding to European Patent Application No. 06789107.7 date May 23, 2008.

European Communication corresponding to European Patent Application No. 06789107.7 date Jun. 18, 2010.

Office Communication dated Dec. 14, 2010, corresponding to European Patent Application No. 06789107.7.

Office Communication mailed Oct. 11, 2011, corresponding to Japanese Patent Application No. 2008-524278.

Office Communication corresponding to Canadian Patent Application No. 2,615,627 dated Oct. 31, 2012.

* cited by examiner

METHODS FOR PREPARING POLYMERIC REAGENTS AND COMPOSITIONS OF POLYMERIC REAGENTS

CROSS REFERENCE TO RELATED APPLICATIONS

This application is a continuation of U.S. patent application Ser. No. 12/820,124, filed Jun. 21, 2010, now U.S. Pat. No. 8,193,306, which application is a continuation of U.S. patent application Ser. No. 11/497,463, filed Jul. 31, 2006, now U.S. Pat. No. 7,767,784, which application claims the benefit of priority to U.S. Provisional Patent Application Ser. No. 60/703,709, filed Jul. 29, 2005, the contents of which are incorporated herein by reference in their entireties.

FIELD OF THE INVENTION

This invention relates to methods for preparing water soluble and non-peptidic polymers ("polymeric reagents") as well as to compositions of water-soluble of the same, conjugates, pharmaceutical compositions, and methods of administering pharmaceutical compositions.

BACKGROUND OF THE INVENTION

Scientists and clinicians face a number of challenges in their attempts to develop active agents into forms suited for delivery to a patient. Active agents that are proteins, for example, are often delivered via injection rather than orally. In this way, the protein is introduced into the systemic circulation without exposure to the proteolytic environment of the stomach. Injection of proteins, however, has several drawbacks. For example, many proteins have a relatively short half-life, thereby necessitating repeated injections, which are often inconvenient and painful. Moreover, some proteins may elicit one or more immune responses with the consequence that the patient's immune system attempts to destroy or otherwise neutralize the immunogenic protein. Of course, once the protein has been destroyed or otherwise neutralized, the protein cannot exert its intended pharmacodynamic activity. Thus, delivery of active agents such as proteins is often problematic even when these agents are administered by injection.

Some success has been achieved in addressing the problems of delivering active agents via injection. For example, conjugating an active agent to a water-soluble polymer has resulted in a polymer-active agent conjugate having reduced immunogenicity and antigenicity. In addition, the polymer-active agent conjugate often has an increased half-life compared to its unconjugated counterpart as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits with a health care professional. Moreover, active agents that were only marginally soluble demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kennilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been PEGylated. Harris et al. have provided a review of the effects of PEGylation on pharmaceuticals. Harris et al. (2003) *Nat. Rev. Drug Discov.* 2(3):214-221.

Typically, the formation of a conjugate involves reaction between an active agent and a polymeric reagent. While small scale amounts of polymeric reagents are available from commercial sources such as Nektar Therapeutics, a concern arises when a commercial or production scale of the polymeric reagent is required. In particular, there is a concern that the particular polymeric reagent used in making the desired conjugate (or an intermediate useful in preparing the polymeric reagent used in making the desired conjugate) cannot be synthesized, largely free of potentially harmful impurities, in a timely, efficient, and economical manner.

For example, the conventional synthesis of polymers bearing an active ester—which can be used a polymeric reagent as well as an intermediate useful in preparing other polymeric reagents—requires an excess of a low molecular weight reagent [such as di(1-benzotriazolyl)carbonate], which must be removed. Although complicated, removal of the low molecular weight reagent is necessary so that the low molecular weight reagent does not react with other molecules, thereby introducing undesired side reactions and products that result in a relatively impure product and decreased yield.

In one approach for preparing polymers bearing an active ester, U.S. Pat. No. 6,624,246 describes the synthesis of methoxy poly(ethylene glycol) bearing a benzotriazole carbonate group ("mPEG-BTC"). As described therein, the process effectively involves mPEG-BTC formation followed by mPEG-BTC purification to purify the mPEG-BTC species and remove unreacted di(1-benzotriazolyl)carbonate and any other low molecular weight products (e.g., 1-benzotriazolyl alcohol). As described in U.S. Pat. No. 6,624,246, the purification of mPEG-BTC involves multiple precipitation steps. A schematic of the process is provided below.

A) mPEG-BTC Formation mPEG-OH +

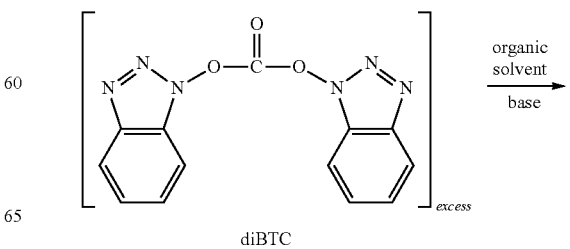

diBTC

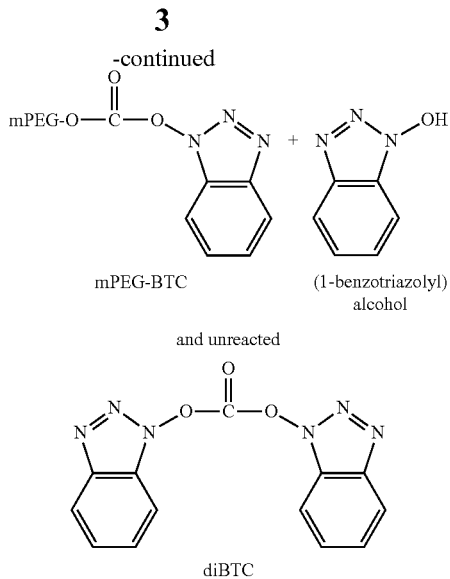

mPEG-BTC     (1-benzotriazolyl) alcohol and unreacted diBTC

B) mPEG-BTC Purification
a) distill off the organic solvent to form a residue of the three products
b) re-dissolve the three products in methylene chloride
c) add ethyl ether, cool and form a precipitate of

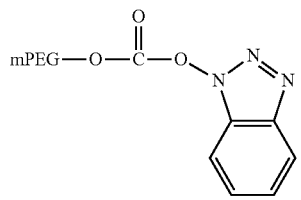

In the manufacture of mPEG-BTC wherein the poly(ethylene glycol) portion has a weight-average molecular weight of about 20,000 Daltons, an eight-fold excess of diBTC was used in order to achieve 100% conversion of all mPEG-OH to mPEG-BTC. Although the large amount of diBTC ensures optimal conversion to MPEG-OH to mPEG-BTC, a relatively large amount of diBTC remains unreacted and must be removed prior to carrying out any further synthetic steps. Otherwise, the remaining diBTC would react with any reactive group (e.g., alcohol group, amine group, and so forth) encountered and introduce undesired impurities and reduce the overall yield.

As described in U.S. Pat. No. 5,932,462, mPEG-BTC was reacted with lysine (bearing two amino groups and a single carboxylic acid group), thereby providing a "lysine branched" structure wherein an mPEG residue is attached at each of the amino groups and the carboxylic acid is available for further functionalizing. While it is conceivable to consume any excess diBTC with adding an excess of lysine, such an approach is flawed for at least two reasons. First, both the diBTC and mPEG-BTC will "compete" for the available lysine amino groups, thereby resulting in a mixture of the desired lysine branched structure and another species having only a single mPEG residue, a single BTC group, and a single carboxylic acid. Second, even if this approach was successful, it would not address situations where a non-lysine residue-containing product is desired.

One may avoid having excess diBTC during the lysine reaction only by destroying the excess diBTC from formation of mPEG-BTC during mPEG-BTC purification. Isopropyl alcohol (IPA, isopropanol) may be substituted for ethyl ether to precipitate the mPEG-BTC from a methylene chloride solution [i.e., e.g., step B(c) in the above schematic]. If this change is made, the IPA reacts with the excess diBTC to form isopropyl-BTC, which is soluble in the mixture of methylene chloride and IPA. Unfortunately, in such an operation at large scale, some isopropyl-BTC is trapped in the mPEG-BTC precipitate. Since the isopropyl-BTC would compete with mPEG-BTC in any reaction with lysine, the isopropyl-BTC must be removed before manufacturing can continue. To remove the trapped isopropyl-BTC, one or two additional "re-precipitation" steps must be carried out in order to get mPEG-BTC free of isopropyl-BTC. As each re-precipitation gives some loss of the mPEG-BTC product because only about 85-95% of the solid can be recovered, this approach is costly and requires additional time.

In another approach for preparing polymers bearing an active ester, U.S. Pat. No. 5,281,698 describes the synthesis of methoxy poly(ethylene glycol) bearing a succinimide carbonate group ("mPEG-SC"). As described therein, the process effectively involves mPEG-SC formation followed by mPEG-SC purification to purify the mPEG-SC species and remove unreacted disuccinimidyl carbonate and any other low molecular weight products (e.g., N-hydroxysuccinimide). As described in U.S. Pat. No. 5,281,698, the purification of mPEG-SC involves filtration and multiple precipitation steps. A schematic of the process is provided below.

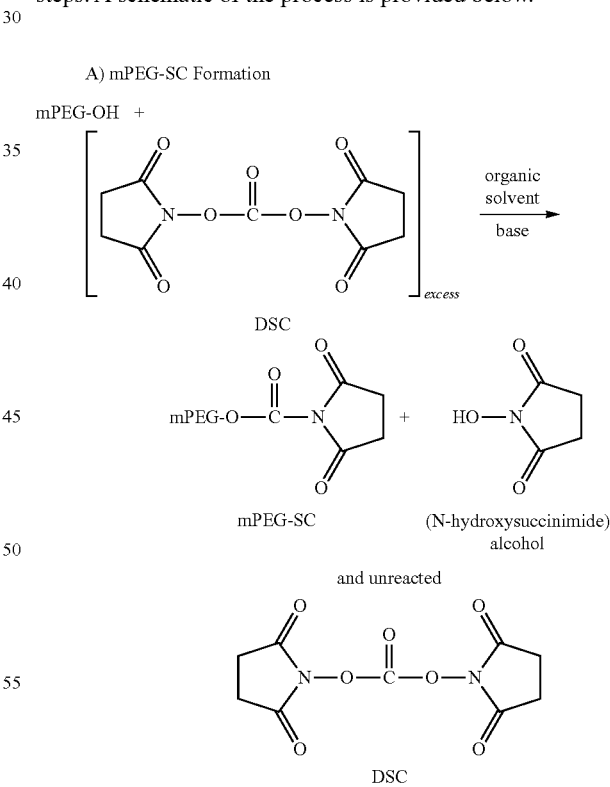

B) mPEG-SC Purification
a) filter the reaction mixture
b) distill off the organic solvent to form a residue of the three products
c) re-dissolve the three products in methylene chloride
d) add ethyl ether, cool and form a precipitate of mPEG-SC
f) repeat precipitation (step c and d) two more times In the manufacture of mPEG-SC wherein the poly(ethylene glycol) portion has a weight-average molecular weight of about 6100 Daltons, an twenty-fold excess of DSC was used in order to achieve 100% conversion of all mPEG-OH to mPEG-SC. Although the large amount of DSC ensures optimal conversion to MPEG-OH to mPEG-SC, a relatively large amount of DSC remains unreacted and must be removed prior to carrying out any further synthetic steps. Otherwise, the remaining DSC would react with any reactive group (e.g., alcohol group, amine group, and so forth) encountered and introduce undesired impurities and reduce the overall yield.

Thus, there remains a need for an efficient method to remove excess low molecular weight reagents, such as diBTC and/or its reactive degradants, from the same reaction mixture in which the low molecular weight reagent was added, thereby resulting in a "one-pot" reaction. This present invention addresses this and other needs in the art.

SUMMARY OF THE INVENTION

In one or more embodiments, a synthetic method is provided, the method comprising:

(a) combining a composition comprising an amine-terminated or hydroxy-terminated, water-soluble polymer with a composition comprising an activated carbonate reagent, optionally in the presence of a catalyst or acid-neutralizing base, wherein the composition comprising the activated carbonate reagent is added such that there is an excess of the activated carbonate reagent relative to the amine-terminated or hydroxy-terminated, water-soluble polymer, to thereby result in a composition comprising an active carbonate ester of the water-soluble polymer and unreacted activated carbonate reagent; and (b) adding a composition comprising a reactive molecule to the composition comprising the active carbonate ester of the water-soluble polymer and unreacted activated carbonate reagent, wherein the composition comprising a reactive molecule is added such that substantially all of the unreacted activated carbonate reagent is substantially consumed.

In one or more embodiments of invention, a synthetic method is provided, the method comprising:

(a) combining a composition comprising a hydroxy-terminated, water-soluble polymer having the following structure:

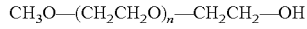

wherein (n) is an integer from 2 to about 4000, with a composition comprising di(1-benzotriazolyl)carbonate, wherein the composition comprising the di(1-benzotriazolyl)carbonate is added such that there is an excess of the di(1-benzotriazolyl)carbonate relative to the hydroxy-terminated, water-soluble polymer, to thereby result in a composition comprising an active carbonate ester of the water-soluble polymer having the following structure:

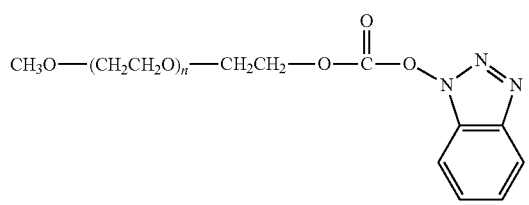

wherein (n) is an integer from 2 to about 4000, and unreacted di(1-benzotriazolyl)carbonate;

(b) adding a composition comprising a reactive molecule to the composition comprising the active carbonate ester of a water-soluble polymer and unreacted di(1-benzotriazolyl) carbonate, wherein the composition comprising the reactive compound is added such that substantially all of the unreacted di(1-benzotriazolyl)carbonate is substantially consumed.

In one or more embodiments of the invention, a synthetic method is provided, the method comprising:

(a) combining a composition comprising a hydroxy-terminated, water-soluble polymer having the following structure:

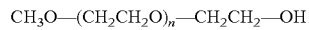

wherein (n) is an integer from 2 to about 4000, with a composition comprising disuccinimidyl carbonate, wherein the composition comprising the disuccinimidyl carbonate is added such that there is an excess of the disuccinimidyl carbonate relative to the hydroxy-terminated, water-soluble polymer, to thereby result in a composition comprising an active carbonate ester of the water-soluble polymer having the following structure:

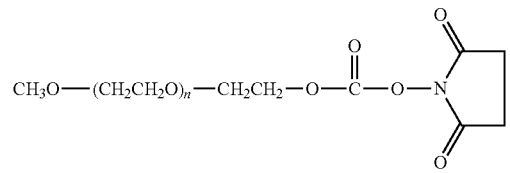

wherein (n) is an integer from 2 to about 4000, and unreacted disuccinimidyl carbonate;

(b) adding a composition comprising a reactive molecule to the composition comprising the active carbonate ester of the water-soluble polymer and unreacted disuccinimidyl carbonate, wherein the composition comprising the reactive molecule is added such that substantially all of the unreacted disuccinimidyl carbonate is substantially consumed.

In one or more embodiments of the invention, a synthetic method is provided, the method comprising:

(a) combining a composition comprising a hydroxy-terminated, water-soluble polymer having the following structure:

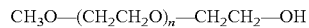

wherein (n) is an integer from 2 to about 4000, with a composition comprising p-nitrophenyl chloroformate, wherein the composition comprising the p-nitrophenyl chloroformate is added such that there is an excess of the p-nitrophenyl chloroformate relative to the hydroxy-terminated, water-soluble polymer, to thereby result in a composition comprising an active carbonate ester of the water-soluble polymer having the following structure:

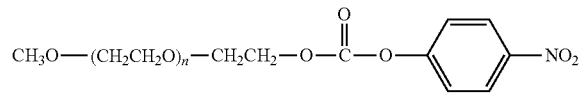

wherein (n) is an integer from 2 to about 4000, and unreacted p-nitrophenyl chloroformate;

(b) adding a composition comprising a reactive molecule to the composition comprising the active carbonate ester of water-soluble polymer and unreacted p-nitrophenyl chloroformate, wherein the composition comprising the reactive molecule is added such that substantially all of the unreacted p-nitrophenyl chloroformate is substantially consumed.

In one or more embodiments of the invention, a synthetic method is provided, the method comprising:

reacting an active carbonate ester of a water-soluble polymer prepared by
(i) combining a composition comprising an amine-terminated or hydroxy-terminated, water-soluble polymer with a composition comprising an activated carbonate reagent, optionally in the presence of a catalyst or acid-neutralizing base, wherein the composition comprising the activated carbonate reagent is added such that there is an excess of the activated carbonate reagent relative to the amine-terminated or hydroxy-terminated, water-soluble polymer, to thereby result in a composition comprising an active carbonate ester of the water-soluble polymer and unreacted activated carbonate reagent; and
(ii) adding a composition comprising a reactive molecule to the composition comprising the active carbonate ester of the water-soluble polymer and unreacted activated carbonate reagent, wherein the composition comprising a reactive molecule is added such that substantially all of the unreacted activated carbonate reagent is substantially consumed,
with an active agent under conjugation conditions to thereby result in a water-soluble polymer-active agent conjugate.

In one or more reacting a polymeric reagent prepared by
(a) combining a composition comprising an amine-terminated or hydroxy-terminated, water-soluble polymer with a composition comprising an activated carbonate reagent, optionally in the presence of a catalyst or acid-neutralizing base, wherein the composition comprising the activated carbonate reagent is added such that there is an excess of the activated carbonate reagent relative to the amine-terminated or hydroxy-terminated, water-soluble polymer, to thereby result in a composition comprising an active carbonate ester of the water-soluble polymer and unreacted activated carbonate reagent;
(b) adding a composition comprising a reactive molecule to the composition comprising the active carbonate ester of the water-soluble polymer and unreacted activated carbonate reagent, wherein the composition comprising a reactive molecule is added such that substantially all of the unreacted activated carbonate reagent is substantially consumed; and
(c) reacting the active carbonate ester of the water-soluble polymer in one or more reactions to form a polymeric reagent
with an active agent under conjugation conditions to thereby result in a water-soluble polymer-active agent conjugate.

In one or more embodiments of the invention, a synthetic method is provided, the method comprising:
reacting a polymeric reagent prepared by
(a) combining a composition comprising an amine-terminated or hydroxy-terminated, water-soluble polymer with a composition comprising an activated carbonate reagent, optionally in the presence of a catalyst or acid-neutralizing base, wherein the composition comprising the activated carbonate reagent is added such that there is an excess of the activated carbonate reagent relative to the amine-terminated or hydroxy-terminated, water-soluble polymer, to thereby result in a composition comprising an active carbonate ester of the water-soluble polymer and unreacted activated carbonate reagent;
(b) adding a composition comprising a reactive molecule to the composition comprising the active carbonate ester of the water-soluble polymer and unreacted activated carbonate reagent, wherein the composition comprising a reactive molecule is added such that substantially all of the unreacted activated carbonate reagent is substantially consumed; and
(c) reacting the active carbonate ester of the water-soluble polymer in one or more reactions to form a polymeric reagent
with an active agent under conjugation conditions to thereby result in a water-soluble polymer-active agent conjugate.

In one or more embodiments of the invention, a method for preparing a conjugate-containing composition is provided, the method comprising combining an active carbonate ester of a water soluble polymer or (polymeric reagent prepared therefrom) as prepared according to a synthetic method described herein with an active agent to thereby result in a conjugate-containing composition.

In one or more embodiments of the invention, a conjugate-containing composition is provided, the composition resulting from the method for preparing a conjugate-containing composition as provided herein.

DETAILED DESCRIPTION OF THE INVENTION

Before describing one or more embodiments of the present invention in detail, it is to be understood that this invention is not limited to the particular polymers, reagents, and the like, as such may vary.

It must be noted that, as used in this specification and the claims, the singular forms "a," "an," and "the" include plural referents unless the context clearly dictates otherwise. Thus, for example, reference to "a polymer" includes a single polymer as well as two or more of the same or different polymers, reference to "an activated carbonate reagent" refers to a single activated carbonate reagent as well as two or more of the same or different activated carbonate reactive agents, and the like.

In describing and claiming the present invention(s), the following terminology will be used in accordance with the definitions provided below.

"PEG," "polyethylene glycol" and "poly(ethylene glycol)" as used herein, are interchangeable. Typically, PEGs for use in accordance with the invention comprise the following structure: "—$(OCH_2CH_2)_n$—" where (n) is 2 to 4000. As used herein, PEG also includes "—$CH_2CH_2$—O$(CH_2CH_2O)_n$—$CH_2CH_2$—" and "(—$OCH_2CH_2)_nO$—," depending upon whether or not the terminal oxygens have been displaced. Throughout the specification and claims, it should be remembered that the term "PEG" includes structures having various terminal or "end capping" groups. The term "PEG" also means a polymer that contains a majority, that is to say, greater than 50%, of —$OCH_2CH_2$— or —$CH_2CH_2O$-repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The terms "active" or "activated" when used in conjunction with a particular functional group, refer to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" or "linker" are used herein to refer to an atom or a collection of atoms used to link interconnecting moieties such as a terminus of a polymer and an active agent or an electrophile or nucleophile of an active agent. The spacer moiety may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched. Non-limiting examples of lower alkyl include methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl, substituted alkyl [preferably $C_{1-6}$ alkyl (e.g., methoxy, ethoxy, propyloxy, and so forth) or $C_{1-6}$ substituted alkyl], aryl, substituted aryl, The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy; lower phenyl; substituted phenyl; nitro, and the like. "Substituted aryl" is aryl having one or more noninterfering substituents. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl and substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucelophilic group" refers to an ion or atom or collection of atoms that may be ionic having a nucleophilic center, i.e., a center that is seeking an electrophilic center or capable of reacting with an electrophile.

A "physiologically cleavable" or "hydrolyzable" bond is a bond that reacts with water (i.e., is hydrolyzed) under physiological conditions. Preferred are bonds that have a hydrolysis half-life at pH 8, 25° C. of less than about 30 minutes. The tendency of a bond to hydrolyze in water will depend not only on the general type of linkage connecting two given atoms but also on the substituents attached to these two given atoms. Appropriate hydrolytically unstable or weak linkages include but are not limited to carboxylate ester, phosphate ester, anhydrides, acetals, ketals, acyloxyalkyl ether, imine, orthoester, peptide and oligonucleotide.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethane, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" refers to an excipient that may optionally be included in a composition and that causes no significant adverse toxicological effects to a patient upon administration.

"Therapeutically effective amount" is used herein to mean the amount of a conjugate that is needed to provide a desired level of the conjugate (or corresponding unconjugated active agent) in the bloodstream or in the target tissue. The precise amount will depend upon numerous factors, e.g., the particular active agent, the components and physical characteristics of the therapeutic composition, the intended patient population, the mode of delivery, individual patient considerations, and the like, and can readily be determined by one skilled in the art.

"Multi-functional" means a polymer having three or more functional groups contained therein, where the functional groups may be the same or different. Multi-functional polymeric reagents will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

"Optional" or "optionally" means that the subsequently described circumstance may or may not occur, so that the description includes instances where the circumstance occurs and instances where it does not.

"Substantially" (unless specifically defined for a particular context elsewhere or the context clearly dictates otherwise) means nearly totally or completely, for instance, satisfying one or more of the following: greater than 50%, 51% or greater, 75% or greater, 80% or greater, 90% or greater, and 95% or greater of the condition.

The phrase "substantially nonaqueous" means a composition or reaction medium: (i) having less than 10,000 parts per million of water (less than 1%), more preferably having less than 1,000 parts per million of water (less than 0.1%), still more preferably less than 100 parts per million of water (less than 0.01%), still more preferably less than 10 parts per million of water (less than 0.001%). Preferably, but not necessarily, substantially nonaqueous conditions includes an inert atmosphere.

The term "consumed" as used herein will refer to neutralizing an unreacted activated carbonate reagent [such as di(1-benzotriazolyl)carbonate] using a reactive molecule, which may optionally be a moiety bound on a resin or column, to chemically destroy all or most of the unreacted activated carbonate reagent in a chemical process.

"One pot", as in a one pot synthetic method, means that products from a previous reaction need not be isolated prior to conducting a subsequent reaction.

Unless the specifically stated to the contrary, the term "combining," as in "combining" two or more compositions together as part of a synthetic method, is not limited with respect to the order of addition.

An "activated carbonate" includes diBTC as well di(1-benzotriazolyl)carbonate (BTC), disuccinimidyl carbonate ("DSC"), p-nitrophenyl haloformate, disuccinimidyl oxalate, and triphosgene even though one or more of compounds may not be true "carbonates," (wherein halo is selected from the group consisting of fluoro, chloro, bromo, iodo) and alkoxy-substitutions of one or both of the benzotriazolyl moieties within diBTC. An activated carbonate must, however, result in an activated urethane-, carbonate-, or thiocarbonate-terminated, water-soluble polymer upon reaction with an amine-terminated, hydroxyl-terminated, or thiol-terminated, water-soluble polymer. An activated urethane-, carbonate-, or thiocarbonate-terminated, water-soluble polymer, in turn, is a urethane-, carbonate-, or thiocarbonate-terminated, water-soluble polymer that can react with either a protein or with a reagent to result in a reactive group-terminated, water-soluble polymer.

Unless the context clearly dictates otherwise, when the term "about" precedes a numerical value, the numerical value is understood to mean ±10% of the stated numerical value.

The Steps of the Synthetic Method

The synthetic method includes the following steps:

(a) combining a composition comprising an amine-terminated or hydroxy-terminated, water-soluble polymer with a composition comprising an activated carbonate reagent, optionally in the presence of a catalyst or acid-neutralizing base, wherein the composition comprising the activated carbonate reagent is added such that there is an excess of the activated carbonate reagent relative to the amine-terminated or hydroxy-terminated, water-soluble polymer, to thereby result in a composition comprising an active carbonate ester of the water-soluble polymer and unreacted activated carbonate reagent; and (b) adding a composition comprising a reactive molecule to the composition comprising the active carbonate ester of the water-soluble polymer and unreacted activated carbonate reagent, wherein the composition comprising a reactive molecule is added such that substantially all of the unreacted activated carbonate reagent is substantially consumed.

The combining step results in the formation of, among other things, a composition comprising an active urethane-, carbonate- or thiol-terminated, water-soluble polymer. A urethane-terminated, water-soluble polymer is formed when a composition comprising an amine-terminated, water-soluble polymer is used. A carbonate-terminated, water-soluble polymer is formed when a composition comprising a hydroxyl-terminated, water-soluble polymer is used. A thiocarbonate-terminated, water-soluble polymer is formed when a thiol-terminated, water-soluble polymer is used. Each of these so-formed water-soluble polymers (i.e., the urethane-terminated, water-soluble polymer, the carbonate-terminated, water-soluble polymer, and the thiocarbonate-terminated, water-soluble polymer) the prepared as part of the methods provided herein will be referred to as an active carbonate ester of the water-soluble polymer.

The method of the invention is schematically provided below, wherein a composition comprising the hydroxyl-terminated, water-soluble polymer mPEG-OH is used, the activated carbonate reagent is di(1-benzotriazolyl)carbonate, the resulting active carbonate ester is mPEG-BTC, and the reactive molecule is water.

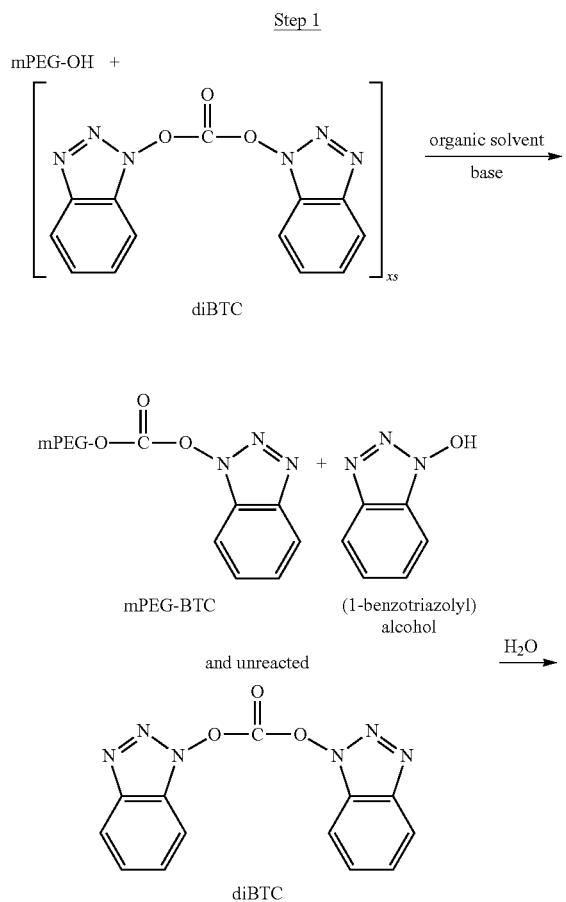

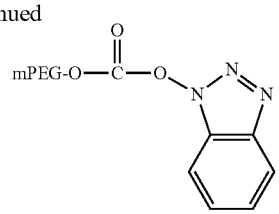

mPEG-BTC and

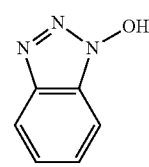

(1-benzotriazolyl) alcohol and $CO_2$

Thus, in an exemplary approach, the method comprises a) combining a composition comprising a hydroxy-terminated, water-soluble polymer of the following structure: POLY-$(X)_a$—OH, wherein POLY is a water-soluble polymer, X (when present) is an optional spacer moiety, (a) is either zero or one [preferably, POLY-$(X)_a$—OH is $CH_3O$—$(CH_2CH_2O)_n$—$CH_2CH_2$—OH], with a composition comprising di(1-benzotriazolyl)carbonate, wherein the composition comprising the di(1-benzotriazolyl)carbonate is added such that there is an excess of the di(1-benzotriazolyl) relative to the hydroxy-terminated, water-soluble polymer, to thereby result in a composition comprising an active carbonate ester of a water-soluble polymer having the following structure:

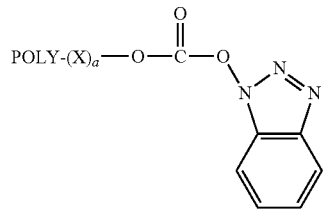

wherein POLY, X and (a) are as previously defined, preferably

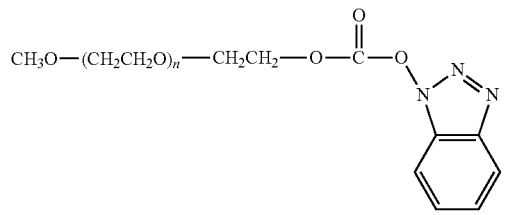

wherein (n) is an integer from 2 to about 4000, and unreacted di(1-benzotriazolyl)carbonate (and liberated hydroxybenzotriazole);

b) adding water to the composition comprising the active carbonate ester of the water-soluble polymer and unreacted di(1-benzotriazolyl)carbonate, wherein the water is added such that substantially all of the unreacted activated carbonate reagent is substantially consumed.

The method can advantageously be carried out as a "one-pot" synthesis. In addition, the method does not require a precipitation step to remove the activated carbonate reagent as required in the method disclosed in U.S. Pat. No. 6,624,246. However, if this activated carbonate reagent is the reagent desired, it may be isolated by precipitation.

Optionally, the method further comprises reacting the active carbonate ester of a water soluble polymer (such as mPEG-BTC) in one or more reactions to form a different polymeric reagent. Having formed a polymeric reagent, it is possible to react the polymeric reagent with an active agent under conjugation conditions to thereby result in a water-soluble polymer-active agent conjugate. While the active carbonate ester of the water soluble polymer (such as mPEG-BTC) can be used as an intermediate in the formation of a polymeric reagent, it is also possible to use the active carbonate ester (such as mPEG-BTC) itself as a polymeric reagent in a conjugation reaction.

In order to recover active carbonate esters of water-soluble polymers, it is typical to add an excess of a non-solvent. Examplary non-solvents include isopropyl alcohol, diethyl ether, MTBE, heptane, THF, hexane, and combinations thereof.

In one or more embodiments of the invention, the active carbonate ester of the water-soluble polymer will have a structure of the following formula:

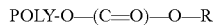

wherein:
POLY is a water-soluble polymer; and
R is an organic radical,
with the proviso that when POLY is a linear, methyl-capped poly(ethylene glycol), the linear, methyl-capped polyethylene glycol has a molecular weight of at least 103.

Exemplary reactive molecules for use in the method include nucleophilic molecules such as water, lower alkyl monohydric alcohols (such as methanol, ethanol, n-propanol, isopropanol, and so forth), lower alkyl monobasic amines, and resins bearing bound reactive carboxylate, hydroxyl, thiol or amine groups (via, for example, an amine gel, such as a Duolite A-7 amine gel). Advantageously, such resin can form part of a column through which a composition bearing unreacted activated carbonate reagent can be passed to effect the step of "adding a composition comprising a reactive molecule to the composition comprising an active carbonate ester of the water-soluble polymer and unreacted activated carbonate reagent"). It is preferred, however, that the reactive molecule is water. Water can be added directly. In addition, water can be added via a moiety that releases water, such a hydrated salt.

In one or more embodiments of the method, the formation of carbon dioxide results upon the unreacted activated carbonate reagent being substantially consumed.

The combining step requires, as a composition comprising an amine-terminated, hydroxy-terminated, or thiol-terminated, water-soluble polymer. As used herein, an "amine-terminated, hydroxy-terminated or thiol-terminated, water-soluble polymer" is any water-soluble polymer that bears at least one amine group ("—NH$_2$") or hydroxy group ("—OH"), or thiol group ("—SH"), regardless of whether the amine group, hydroxy group or thiol group is actually located at a terminus of the water-soluble polymer. In fact, the amine group (—NH$_2$) or hydroxy group ("OH") or thiol group ("—SH") may be bound to an aromatic group.

The combining step also requires a composition comprising an activated carbonate reagent. The activated carbonate reagent use in the method is typically, although not necessarily, selected from the group consisting of di(1-benzotriazolyl) carbonate (BTC), disuccinimidyl carbonate ("DSC"), p-nitrophenyl chloroformate, trichlorophenyl chloroformate, p-nitrophenyl succinimidyl carbonate, p-nitrophenyl 1-benzotriazolyl carbonate, pentafluorophenyl chloroformate, 1,1'-carbonyldiimidazole, disuccinimidyl oxalate, and triphosgene. In certain instances, the activated carbonate reagent has a structure of one of the following formulae: R—O(C=O)—OR; R—O(C=O)—OR'; and R—O(C=O)X, wherein R is an organic radical, R' is an organic radical different than R, and X is Cl, Br, or I.

The excess of the activated carbonate reagent relative to the amine-terminated or hydroxy-terminated, water-soluble polymer represents one or more of the following: at least about 5 mol % excess, at least about 50 mol % excess, at least about a two molar excess; at least about a four molar excess; and at least about an eight molar excess.

The method for preparing active carbonate esters of water-soluble polymers has utility as, among other things, providing an intermediate that is useful in the formation of polymeric reagents, as discussed in, for example, U.S. Pat. Nos. 6,624,246, and 5,932,462.

The combining step is typically carried out under substantially nonaqueous conditions. In addition, aprotic solvent-based compositions are used in the synthetic methods. In addition, the entire synthetic approach is often carried out under an inert atmosphere, such as argon.

One or more of the steps of the method are carried out in an organic solvent. Although any organic solvent can be used and the invention is not limited in this regard, exemplary organic solvents include those solvents selected from the group consisting of halogenated aliphatic hydrocarbons, alcohols, aromatic hydrocarbons, halogenated aromatic hydrocarbons, ethers, cyclic ethers, and combinations thereof Examples of preferred organic solvents include those selected from the group consisting of methylene chloride (dichloromethane), chloroform, octanol, toluene, methyl t-butyl ether, tetrahydrofuran, ethyl acetate, diethylcarbonate, acetone, acetonitrile, DMF, DMSO, dimethylacetamide, N-cyclohexylpyrrolidinone, cyclohexane and combinations thereof.

Method for Preparing a Conjugate-Containing Composition

In one or more embodiments of the invention, a method for preparing a conjugate-containing composition is provided, the method comprising combining an active agent with an active carbonate ester of a water-soluble polymer (or a polymeric reagent that was prepared using such an active carbonate ester of a water-soluble polymer) to thereby result in a conjugate-containing composition. Thus, included within the invention are methods for preparing conjugate-containing compositions.

Conjugate-Containing Compositions

In one or more embodiments of the invention, a conjugate-containing composition is provided, the composition resulting from the method comprising combining an active agent with an active carbonate ester of a water-soluble polymer (or a polymeric reagent that was prepared using such an active carbonate ester of a water-soluble polymer) as provided herein.

Thus, included within the invention are conjugate-containing compositions. The compositions (both conjugate compositions and reagent compositions) are believed to have greater purity than previously known methods and also more efficiently prepared.

The Water-Soluble Polymer ("POLY")

As used herein, the term "water soluble polymer" includes those water soluble polymers that are biocompatible and non-immunogenic and specifically excludes any water soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water soluble polymer segments described herein as well as conjugates are biocompatible and nonimmunogenic.

When referring to the polymer, it is to be understood that the polymer can be any of a number of water soluble and non-peptidic polymers, such as those described herein as suitable for use in the present invention. Preferably, poly (ethylene glycol) (i.e., PEG) is the polymer. The term PEG includes poly(ethylene glycol) in any of a number of geometries or forms, including linear forms, branched or multi-arm forms (e.g., forked PEG or PEG attached to a polyol core), pendant PEG, or PEG with degradable linkages therein, to be more fully described below.

The number of functional groups carried by the polymer and the position of the functional groups may vary. Typically, the polymer will comprise 1 to about 25 functional groups, preferably 1, 2, 3, 4, 5, 6, 7, 8, 9, or 10 functional groups. Linear polymers, such as PEG polymers, will typically comprise one or two functional groups positioned at the terminus of the polymer chain. If the PEG polymer is monofunctional (i.e., mPEG), the polymer will include a single functional group. If the PEG polymer is difunctional, the polymer may contain two independently selected functional groups, one at each terminus of the polymer chain. As would be understood, multi-arm or branched polymers may comprise a greater number of functional groups.

Multi-armed or branched PEG molecules, such as those described in U.S. Pat. No. 5,932,462, which is incorporated by reference herein in its entirety, can also be used as the PEG polymer. Generally speaking, a multi-armed or branched polymer possesses two or more polymer "arms" extending from a central branch point. For example, an exemplary branched PEG polymer has the structure:

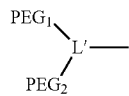

wherein $PEG_1$ and $PEG_2$ are PEG polymers in any of the forms or geometries described herein, and which can be the same or different, and L' is a hydrolytically stable linkage. An exemplary branched PEG has the structure:

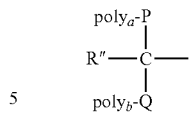

wherein $poly_a$ and $poly_b$ are PEG backbones, such as methoxy poly(ethylene glycol); R" is a nonreactive moiety, such as H, methyl or a PEG backbone; and P and Q are nonreactive linkages. In a preferred embodiment, the branched PEG polymer is methoxy poly(ethylene glycol) disubstituted lysine. For purposes herein, a multi-arm structure will include three or more branches while a branched structure will include only two branches.

The branched PEG structure can be attached to a third oligomer or polymer chain as shown below:

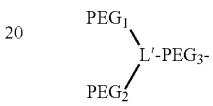

wherein $PEG_3$ is a third PEG oligomer or polymer chain, which can be the same or different from $PEG_1$ and $PEG_2$.

The PEG polymer can alternatively comprise a forked PEG. Generally speaking, a polymer having a forked structure is characterized as having a polymer chain attached to two or more functional groups via covalent linkages extending from a hydrolytically stable branch point in the polymer. An example of a forked PEG is represented by $PEG-YCHZ_2$, where Y is a linking group and Z is an activated terminal group for covalent attachment to a biologically active agent. The Z group is linked to CH by a chain of atoms of defined length. U.S. Pat. No. 6,362,254, the contents of which are incorporated by reference herein, discloses various forked PEG structures capable of use in the present invention. The chain of atoms linking the Z functional groups (e.g., hydroxyl groups) to the branching carbon atom serve as a tethering group and may comprise, for example, an alkyl chain, ether linkage, ester linkage, amide linkage, or combinations thereof The PEG polymer may comprise a pendant PEG molecule having reactive groups (e.g., hydroxyl groups) covalently attached along the length of the PEG backbone rather than at the end of the PEG chain. The pendant reactive groups can be attached to the PEG backbone directly or through a linking moiety, such as an alkylene group.

In addition to the above-described forms of PEG, the polymer can also be prepared with one or more hydrolytically stable or degradable linkages in the polymer backbone, including any of the above described polymers. For example, PEG can be prepared with ester linkages in the polymer backbone that are subject to hydrolysis. As shown below, this hydrolysis results in cleavage of the polymer into fragments of lower molecular weight:

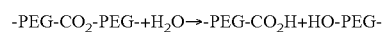

Other hydrolytically degradable linkages, useful as a degradable linkage within a polymer backbone, include carbonate linkages; imine linkages resulting, for example, from reaction of an amine and an aldehyde (see, e.g., Ouchi et al., Polymer Preprints, 38(1):582-3 (1997), which is incorporated herein by reference.); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between acid derivatives and an alcohol; and oligonucleotide linkages formed by, for example, a phosphoramidite group, e.g., at the end of a polymer, and a 5' hydroxyl group of an oligonucleotide. The use of many of the above-described degradable linkages is less preferred due to nucleophilic reactivity of many of the unstable linkages with amine groups.

It is understood by those skilled in the art that the term poly(ethylene glycol) or PEG represents or includes all the above forms of PEG.

Any of a variety of other polymers comprising other non-peptidic and water soluble polymer chains can also be used in the present invention. The polymer can be linear, or can be in any of the above-described forms (e.g., branched, forked, and the like). Examples of suitable polymers include, but are not limited to, other poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly($\alpha$-hydroxyacetic acid), poly(acrylic acid), poly(vinyl alcohol), polyphosphazene, polyoxazolines, poly(N-acryloylmorpholine), such as described in U.S. Pat. No. 5,629,384, which is incorporated by reference herein in its entirety, and copolymers, terpolymers, and mixtures thereof.

Although the molecular weight of the water soluble polymer can vary depending on the desired application, the configuration of the polymer structure, the degree of branching, and the like, the molecular weight will satisfy one or more of the following values: greater than 100 Daltons; greater than 200 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons; greater than 2,200 Daltons; greater than 2,500 Daltons; greater than 3,000 Daltons; greater than 4,000 Daltons; greater than 4,900 Daltons; greater than 5,000 Daltons; greater than 6,000 Daltons; greater than 7,000 Daltons; greater than 7,500 Daltons, greater than 9,000 Daltons; greater than 10,000 Daltons; greater than 11,000 Daltons; greater than 14,000 Daltons; greater than 15,000 Daltons; greater than 16,000 Daltons; greater than 19,000 Daltons; greater than 20,000 Daltons; greater than 21,000 Daltons; greater than 22,000 Daltons; greater than 25,000 Daltons; and greater than 30,000 Daltons. It is understood that the maximum limit of molecular weight for any given water soluble polymer segment useful herein is less than about 300,000 Daltons.

The molecular weight of the polymer will typically fall into at least one of the following ranges: from about 100 Daltons to about 100,000 Daltons; from about 200 Daltons to about 60,000 Daltons; from about 300 Daltons to about 40,000 Daltons.

Exemplary molecular weights for the water soluble polymer segment include about 100 Daltons, about 200 Daltons, about 300 Daltons, about 350 Daltons, about 400 Daltons, about 500 Daltons, about 550 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 50,000 Daltons, about 60,000 Daltons, and about 75,000 Daltons.

With respect to branched versions of the polymer, exemplary ranges of suitable sizes for the total molecular weight of the polymer (as based essentially on the combined weights of the two water soluble polymer portions) include the following: from about 200 Daltons to about 100,000 Daltons; from about 1,000 Daltons to about 80,000 Daltons; from about 2,000 Daltons to about 50,000 Daltons; from about 4,000 Daltons to about 25,000 Daltons; and from about 10,000 Daltons to about 40,000 Daltons. More particularly, total weight average molecular weight of a branched version of the polymer of the invention corresponds to one of the following: 400; 1,000; 1,500; 2,000; 3000; 4,000; 10,000; 15,000; 20,000; 30,000; 40,000; 50,000; 60,000; or 80,000.

With respect to PEG, wherein a structure comprising a repeating ethylene oxide monomer, such as "—($CH_2CH_2O$)$_n$—" or "—($OCH_2CH_2$)$_n$," can be provided, preferred values for (n) include: from about 3 to about 3,000; from about 10 to about 3,000; from about 15 to about 3,000; from about 20 to about 3,000; from about 25 to about 3,000; from about 30 to about 3,000; from about 40 to about 3,000; from about 50 to about 3,000; from about 55 to about 3,000; from about 75 to about 3,000; from about 100 to about 3,000; and from about 225 to about 3,000.

The Spacer Moiety ("X")

Optionally, a spacer moiety is found in the water-soluble polymers and other structures provided herein. Exemplary spacer moieties include the following: —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—

NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, —O—C(O)—CH$_2$—CH$_2$—CH$_2$—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —CH$_2$—CH$_2$—CH$_2$—C(O)—NH—CH$_2$—CH$_2$—NH—C(O)—CH$_2$—CH$_2$—, O—C(O)—NH—[CH$_2$]$_f$—(OCH$_2$CH$_2$)$_n$—, and combinations of two or more of any of the foregoing, wherein (f) is 0 to 6, (n) is 0 to 20 (preferably 0 to 10, e.g., 0, 1, 2, 3, 4, 5, 6, 7, 8, 9 or 10, and more preferably 4). In addition, each of the foregoing carbon-containing spacer moieties can have a branched alkyl group attached thereto. Nonlimiting examples of bivalent cycloalkyl (e.g., cycloalkylene) groups include C$_{3-8}$ cycloalkyl, such as various isomers of cyclopropadiyl (e.g., 1,1-, cis-11,2-, or trans-1,2-cyclopropylene), cyclobutadiyl, cyclopentadiyl, cyclohexadiyl, and cycloheptadiyl. The cycloalkylene group can be substituted with one or more alkyl groups, preferably C$_1$-C$_6$ alkyl groups.

Having formed the active carbonate ester of a water-soluble polymer, the active carbonate ester of a water-soluble polymer can be used "as is" as a polymeric reagent useful for a conjugation reaction with an active agent, or can optionally be further derivatized to form a different polymeric reagent bearing a different reactive group. Preferred reactive groups are selected from the group of electrophiles and nucleophiles. Exemplary reactive groups include hydroxyl (—OH), ester, orthoester, carbonate, acetal, aldehyde, aldehyde hydrate, ketone, vinyl ketone, ketone hydrate, thione, thione hydrate, hemiketal, sulfur-substituted hemiketal, ketal, alkenyl, acrylate, methacrylate, acrylamide, sulfone, amine, hydrazide, thiol, disulfide, thiol hydrate, carboxylic acid, isocyanate, isothiocyanate, maleimide

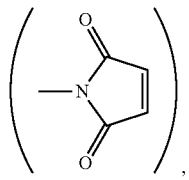

succinimide

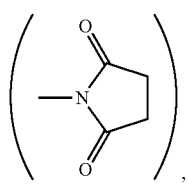

benzotriazole

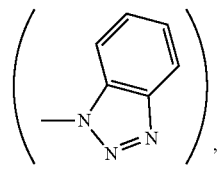

vinylsulfone, chloroethylsulfone, dithiopyridine, vinylpyridine, iodoacetamide, epoxide, glyoxals, diones, mesylates, tosylates, thiosulfonate, tresylate, and silane. Specific examples of preferred reactive groups include amine, carboxylic acid, ester, aldehyde, acetal, succinimide, and maleimide.

Illustrative examples of spacer moieties and reactive group combinations include

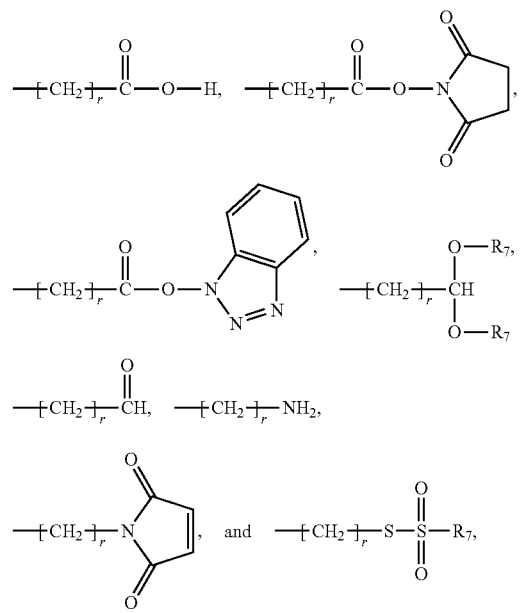

wherein r is 1-5, r' is 0-5, and R$_7$ is aryl or alkyl.

For example, the active carbonate ester of a water-soluble polymer can be reacted with amino acids to form amino acid derivatives. Thus, for example, mPEG-BTC esters can be reacted with lysine to form a polymeric lysine derivative. For example, one such lysine [i.e., H$_2$N(CH$_2$)$_4$CH(NH$_2$)CO$_2$H·HCl] derivative is a doubly PEGylated lysine, wherein the two PEGs are linked to the lysine amines by carbamate bonds, as shown below (wherein n is 2 to about 4000).

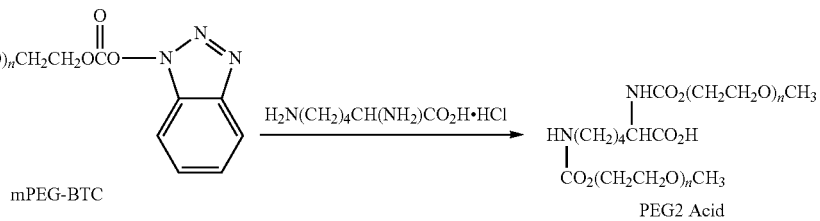

Such PEG derivatives of lysine are useful as reagents for preparation of PEG derivatives of proteins. These PEG derivatives often offer advantages over non-PEGylated proteins, such as longer circulating life-times in vivo, reduced rates of proteolysis, and lowered immunogenicity. In another aspect, PEG BTC derivatives are used directly in attaching PEG to proteins through carbamate linkages and may offer advantages similar to those described for the lysine PEG derivatives.

Thus for example, the above "PEG2 Acid" can be reacted with dicyclohexylcarbodiimide and N-hydroxysuccinimide to form a PEG2 active ester (N-hydroxysuccinimide) of the PEG2 acid. Then, in a subsequent reaction, the PEG2 active ester can be reacted, in the presence of a tertiary amine base, with a trifluoroacetic acid salt of the ethylene diamine monoamide of 3-N-maleimidopropanoic acid to form a polymeric reagent bearing a maleimide group capable of reacting with thiol groups on proteins, bioengineered biomolecules and other therapeutic molecules of interest.

polymer (either prior or subsequent to any deprotection step) so that it bears a specific reactive group. Thus, using techniques well known in the art, the polymer can be functionalized to include a reactive group (e.g., active ester, thiol, maleimide, aldehyde, ketone, and so forth).

For example, when the polymer bears a carboxylic acid as the reactive group, the corresponding ester can be formed using conventional techniques. For example, the carboxylic acid can undergo acid-catalyzed condensation with an alcohol, thereby providing the corresponding ester. One approach to accomplish this is to use the method commonly referred to as a Fischer esterification reaction. Other techniques for forming a desired ester are known by those of ordinary skill in the art.

For example, when the polymer bears a carboxylic acid as the reactive group, the corresponding ester can be formed using conventional techniques. For example, the carboxylic acid can undergo acid-catalyzed condensation with an alcohol, thereby providing the corresponding ester. One approach

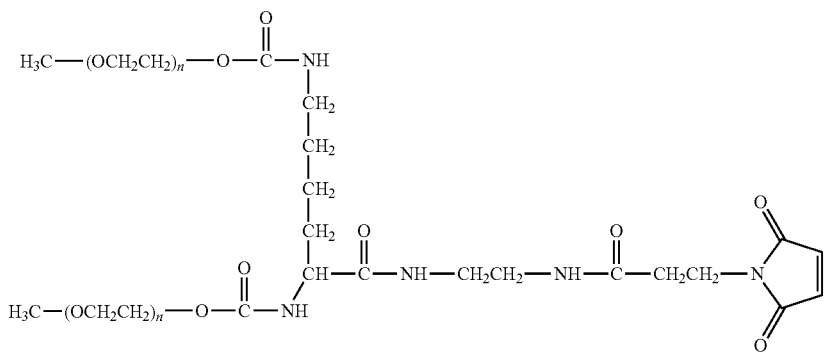

Polymeric Reagent Bearing a Maleimide Group (Wherein n is an Integer from 2 to 4000)

By reacting the above polymeric reagent bearing a maleimide group with a thiol-containing active agent ["(Active Agent)-HS", such as a cysteine-containing polypeptide, protein or other thiol-containing biomolecule] under conjugation reaction conditions, a conjugate having the following structure is formed to accomplish this is to use the method commonly referred to as a Fischer esterification reaction. Other techniques for forming a desired ester are known by those of ordinary skill in the art.

In addition, polymers bearing a carboxylic acid can be modified to form useful reactive groups other than esters. For example, the carboxylic acid can be further derivatized to form acyl halides, acyl pseudohalides, such as acyl cyanide,

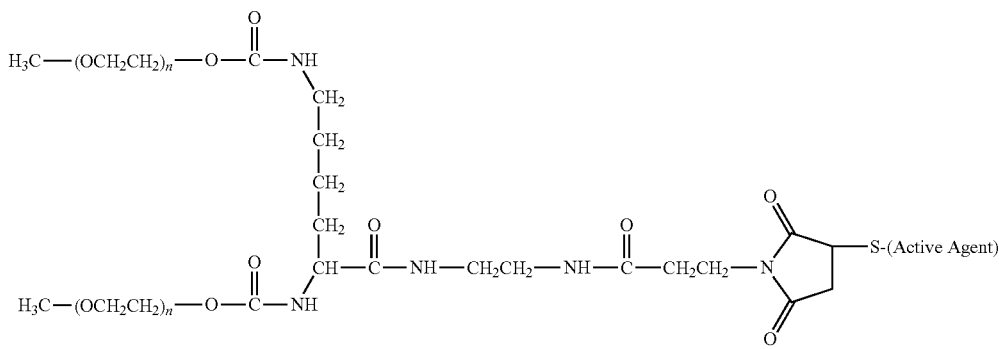

conjugate [wherein n is an integer from 2 to 4000 and "S-(Active Agent) is a residue of the thiol-containing active agent]

Biologically Active Conjugates

For any given polymer, the methods described above advantageously provide the ability to further transform the acyl isocyanate, and acyl azide, neutral salts, such as alkali metal or alkaline-earth metal salts (e.g. calcium, sodium, and barium salts), esters, anhydrides, amides, imides, hydrazides, and the like. In a preferred embodiment, the carboxylic acid is esterified to form an N-succinimidyl ester, o-, m-, or p-nitrophenyl ester, 1-benzotriazolyl ester, imidazolyl ester, or N-sulfosuccinimidyl ester. For example, the carboxylic acid can be converted into the corresponding N-succinimidyl ester by reacting the carboxylic acid with dicyclohexyl carbodiimide (DCC) or diisopropyl carbodiimide (DIC) in the presence of a N-hydroxysuccinimide.

The steps of the synthesis methods described above take place in an appropriate solvent. One of ordinary skill in the art can determine whether any specific solvent is appropriate for any given reaction. Typically, however, the solvent is a nonpolar solvent or a polar aprotic solvent. Nonlimiting examples of nonpolar solvents include benzene, xylene, dioxane, tetrahydrofuran (THF), and toluene. Exemplary polar aprotic solvents include, but are not limited to, acetonitrile, DMSO (dimethyl sulfoxide), HMPA (hexamethylphosphoramide), DMF (dimethylformamide), DMA (dimethylacetamide), and NMP (N-methylpyrrolidinone).

The method of preparing the polymers optionally comprises an additional step of isolating and recovering the polymer once it is formed. Known methods can be used to isolate the polymer, but it is particularly preferred to use chromatography, e.g., size exclusion chromatography. Alternately or in addition, the method includes the step of purifying the polymer once it is formed. Again, standard art-known purification methods can be used to purify the polymer. Isolation of the active carbonate ester of a water-soluble polymer can also be accomplished by distilling off the solvent using art-known methods.

The polymers of the invention can be stored under an inert atmosphere, such as under argon or under nitrogen. In this way, potentially degradative processes associated with, for example, atmospheric oxygen, are reduced or avoided entirely. In some cases, to avoid oxidative degradation, antioxidants, such as butylated hydroxyl toluene (BHT), can be added to the final product prior to storage. In addition, it is preferred to minimize the amount of moisture associated with the storage conditions to reduce potentially damaging reactions associated with water. Moreover, it is preferred to keep the storage conditions dark in order to prevent certain degradative processes that involve light. Thus, preferred storage conditions include one or more of the following: storage under dry argon or another dry inert gas; storage at temperatures below about $-15°$ C.; storage in the absence of light; and storage with a suitable amount (e.g., about 50 to about 500 parts per million) of an antioxidant such as BHT.

The above-described polymers are useful for conjugation to biologically active agents or surfaces comprising at least one group suitable for reaction with the reactive group on the polymer. For example, amino groups (e.g., primary amines), hydrazines, hydrazides, and alcohols on an active agent or surface will react with a carboxylic acid group on the polymer. In addition, a more "activated" version of the carboxylic acid of the polymer can be prepared in order to enhance reactivity to the biologically active agent or surface. Methods for activating carboxylic acids are known in the art and include, for example, the method for forming an active ester described above. Other approaches for activating a carboxylic acid are known to those of ordinary skill in the art.

Typically, the polymer is added to the active agent or surface at an equimolar amount (with respect to the desired number of groups suitable for reaction with the reactive group) or at a molar excess. For example, the polymer can be added to the target active agent at a molar ratio of about 1:1 (polymer:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily, purified to separate out excess reagents, unconjugated reactants (e.g., active agent), undesired multi-conjugated species, and free or unreacted polymer. The resulting conjugates can then be further characterized using analytical methods such as MALDI, capillary electrophoresis, gel electrophoresis, and/or chromatography.

With respect to polymer-active agent conjugates, the conjugates can be purified to obtain/isolate different conjugated species. Alternatively, and more preferably for lower molecular weight (e.g., less than about 20 kiloDaltons, more preferably less than about 10 kiloDaltons) polymers, the product mixture can be purified to obtain the distribution of water-soluble polymer segments per active agent. For example, the product mixture can be purified to obtain an average of anywhere from one to five PEGs per active agent (e.g., protein), typically an average of about 3 PEGs per active agent (e.g., protein). The strategy for purification of the final conjugate reaction mixture will depend upon a number of factors, including, for example, the molecular weight of the polymer employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100 kDa protein is randomly conjugated to a PEG alkanoic acid having a molecular weight of about 20 kDa, the resulting reaction mixture will likely contain unmodified protein (MW 100 kDa), mono-pegylated protein (MW 120 kDa), di-pegylated protein (MW 140 kDa), and so forth. While this approach can be used to separate PEG and other polymer conjugates having different molecular weights, this approach is generally ineffective for separating positional isomers having different polymer attachment sites within the protein. For example, gel filtration chromatography can be used to separate mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content [Sims et al. (1980) *Anal. Biochem,* 107:60-63], and (iv) sodium dodecyl sulfphate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

Following conjugation, and optionally additional separation steps, the conjugate mixture can be concentrated, sterile filtered, and stored at low a temperature, typically from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized powder is absent residual buffer. Alternatively, a buffer exchange step may be used using a formulation buffer, so that the lyophilized conjugate is in a form suitable for reconstitution into a formulation buffer and ultimately for administration to a mammal.

The polymers of the invention can be attached, either covalently or noncovalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymers can also be used in biochemical sensors, bioelectronic switches, and gates. The polymers can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymer as presented herein may be any one or more of the following. hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

Examples of active agents suitable for use in covalent attachment to the reactive polymer of the invention include, but are not limited to, calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX insulin, pro-insulin, insulin analogues (e.g., monoacylated insulin as described in U.S. Pat. No. 5,922,675), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining stability and other parameters of the composition, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with a conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the patient as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains. Although specific terms are employed herein, they are used in a generic and descriptive sense only and not for purposes of limitation.

All articles, books, patents and other publications referenced herein are hereby incorporated by reference in their entireties.

EXPERIMENTAL

The practice of the invention will employ, unless otherwise indicated, conventional techniques of organic synthesis, biochemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level. Each of the following examples is considered to be instructive to one of ordinary skill in the art for carrying out one or more of the embodiments described herein.

Example 1

Preparation of mPEG(5,000 Da)-BTC

A solution of mPEG(5,000 Da)-OH (MW 5,000, 15 g, 0.003 moles), di(1-benzotriazolyl)carbonate (4.0 g of 70% mixture, 0.000945 moles), and pyridine (2.2 ml) in acetonitrile (30 ml) was stirred at room temperature under nitrogen overnight. The NMR analysis showed that the obtained mPEG(5,000 Da)-BTC was 100% substituted and the reaction mixture contained 0.0012 moles of residual di(1-benzotriazolyl)carbonate. A calculated amount of distilled water (0.025 g, calculated to provide an excess amount relative to diBTC) was added and the mixture was stirred for three hours. Consecutive NMR analysis showed that mPEG(5,000 Da)-BTC was still 100% substituted but residual di(1-benzotriazolyl)carbonate was completely hydrolyzed. The solvent was removed by distillation; the residue was dried under vacuum at room temperature to yield 14.8 g of product which was shown by $^1$H NMR analysis to be 100% substituted. Expected $^1$H NMR ($d_6$-DMSO): 3.23 ppm (s, —OCH$_3$, 3H), 3.51 ppm (s, polymer backbone), 4.62 ppm (m, mPEG-O—CH$_2$—OCO$_2$—, 2H), 7.41-8.21 ppm (complex mult, benzotriazole protons, 4H).

Example 2

Preparation of mPEG(20,000 Da)-BTC

A solution of mPEG(20,000 Da)-OH (MW 20,000, 20 g, 0.001 moles), di(1-benzotriazolyl)carbonate (3.4 g of 70% mixture, 0.00803 moles), and pyridine (3.0 ml) in acetonitrile (40 ml) was stirred at room temperature under nitrogen overnight. The NMR analysis showed that the obtained mPEG(20,000 Da)-BTC was 100% substituted and the reaction mixture contained 0.0027 moles of residual di(1-benzotriazolyl)carbonate. A calculated amount of distilled water (0.050 g, calculated to provide an excess amount relative to diBTC) was added and the mixture was stirred for three hours. Consecutive NMR analysis showed that mPEG(20,000 Da) BTC was still 100% substituted but residual di(1-benzotriazolyl)carbonate was completely hydrolyzed. The obtained mixture was used directly to prepare mPEG(20,000 Da)-amine. $^1$H NMR ($d_6$-DMSO): 3.23 ppm (s, —OCH$_3$, 3H), 3.51 ppm (s, polymer backbone), 4.62 ppm (m, mPEG-O—CH$_2$—OCO$_2$—, 2H), 7.41-8.21 ppm (complex mult, benzotriazole protons, 4H).

Example 3

Preparation of mPEG(20,000 Da)-Amine from mPEG(20,000 Da)-BTC

The solution of mPEG(20,000 Da)-benzotriazole carbonate (20.0 g, 0.001 moles) in acetonitrile (40 ml) prepared in Example 2, is added dropwise to the solution of 2,2'-(ethylenedioxy)bis(ethylamine) (Sigma-Aldrich; FW=148.21, 3 g, 0.020 moles) in acetonitrile (40 ml) and the reaction mixture is stirred for two hours at room temperature under argon atmosphere. Next the solvent is evaporated to dryness. The crude product is dissolved in methylene chloride and precipitated with isopropyl alcohol. The wet product is dried under reduced pressure. Yield 18.2 g. Expected $^1$H NMR ($d_6$-DMSO): 2.64 ppm (t, —CH$_2$-amine-, 2H), 3.11 ppm (q, —CH$_2$—NH—,), 3.23 ppm (s, —OCH$_3$, 3H), 3.51 ppm (s, PEG backbone), 4.04 ppm (m, —CH$_2$—O(C=O)—, 2H), 7.11 ppm (t, —(C=O)—NH—, 1H). Cation exchange chromatography: mPEG(20,000 Da)-Amine 97.7%.

Example 4

Preparation of mPEG(20,000 Da)-Succinimidyl Carbonate

A solution of mPEG(20,000 Da)-OH (MW 20,000, 60 g, 0.003 moles), N,N'-disuccinimidyl carbonate (2.4 g, 0.00937 moles), and pyridine (6.5 ml) in acetonitrile (300 ml) was stirred at room temperature under nitrogen overnight. The NMR analysis showed that the obtained mPEG(20,000 Da)-succinimidyl carbonate was 100% substituted and the reaction mixture contained 0.0034 moles of residual N,N'-disuccinimidyl carbonate. A calculated amount of distilled water (0.097 g, calculated to provide an excess amount relative to diBTC) was added and the mixture was stirred for four hours. Consecutive NMR analysis showed that mPEG(20,000 Da)-succinimidyl carbonate was still 100% substituted but residual N,N'-disuccinimidyl carbonate was completely hydrolyzed. The solvent was removed by distillation; the residue was dried under vacuum to yield 56.8 g of product which was shown by $^1$H NMR to be 100% substituted. $^1$H NMR ($d_6$-DMSO): 2.80 ppm (s, succinimide, 4H), 3.23 ppm (s, —OCH₃, 3H), 3.51 ppm (s, polymer backbone), 4.62 ppm (m, mPEG-O—CH₂—OCO₂—, 2H).

Example 5

Preparation of mPEG(20,000 Da)-NPC

A solution of mPEG(20,000 Da)-OH (MW 20,000 Da, 60 g, 0.003 moles), p-nitrophenyl chloroformate (NPC) (1.9 g, 0.00943 moles), and pyridine (6.5 ml) in acetonitrile (300 ml) was stirred at room temperature under nitrogen overnight. The NMR analysis showed that the obtained mPEG(20,000 Da)-NPC was 100% substituted and the reaction mixture contained 0.0034 moles of residual p-nitrophenyl chloroformate. The reaction mixture was passed through gel column (Duolite A-7 amine gel) that allows circulation of small molecules but largely excludes polymeric species. Consecutive NMR analysis showed that mPEG(20,000 Da)-NPC was still 100% substituted but no residual p-nitrophenyl chloroformate. ¹H NMR (CDCl₃): 3.39 ppm (s, —OCH₃, 3H), 3.58 ppm (s, polymer backbone), 4.37 ppm (m, mPEG-O—CH₂—OCO₂—, 2H), 7.44 ppm (m, aromatic protons, 2H), 8.27 ppm (m, aromatic protons, 2H).

Example 6

Preparation of mPEG(22,000 Da)-PropionicAcid from mPEG(20,000 Da)-NPC

To a solution of mPEG(20,000 Da)-NPC (60.0 g, 0.0030 moles from Example 5) in acetonitrile, PEG(2,000 Da)-a-amino-w-propionic acid (6.6 g, 0.0033 moles) and triethylamine (1.8 ml) were added and the reaction mixture was stirred for six hours at room temperature under argon atmosphere. Next, the mixture was filtered and solvent was evaporated to dryness. The crude product was dissolved in methylene chloride and precipitated with isopropyl alcohol. The wet product was dried under reduced pressure. Yield 54.3 g. ¹H NMR (d₆-DMSO): 2.44 ppm (t, —CH₂—COO—, 2H), 3.11 ppm (q, —CH₂—NH—, 2H), 3.24 ppm (s, —OCH₃), 3.51 ppm (s, PEG backbone), 4.04 ppm (m, —CH₂—O(C=O)—, 2H), 7.11 ppm (t, —(C=O)—NH—, 1H). Anion exchange chromatography: M-PEG(20,000 Da)-Propionic Acid 96.5%.

Example 7

Preparation of mPEG(20,000 Da)-BTC

Large Scale Synthesis mPEG(20,000 Da)-OH (28 kg) was dissolved in anhydrous acetonitrile (93 kg) under argon atmosphere. The mixture was dried by passing through a molecular sieves cartridge, then the cartridge was washed with 50 L of acetonitrile. The drying process was repeated until the water content was less than 100 ppm. Di(1-benzotriazolyl)carbonate (1285 g of 42% mixture) was then combined with about 2000 mL of acetonitrile in a separate vessel to form a slurry, which was added under argon to the previously prepared mixture. The separate vessel was rinsed twice with acetonitrile (about 200 mL) to enhance quantitative transfer. Pyridine (200 mL) was then added under argon and followed by mixing at 31° C.±3° C. for 12 hours. Water (about 20 mL), diluted with acetonitrile (1 L), was added and the entire reaction mixture was mixed at 31° C.±3° C. for 60 minutes. Thereafter, the reaction mixture was distilled under reduced pressure and the product was collected and allowed to cool. Isopropanol (551 kg) with a low water content was then added. After addition of the isopropanol was complete, the resulting precipitate was mixed for a minimum of thirty minutes. Thereafter, the precipitate was isolated and washed with isopropanol (about 90 kg) under argon. Finally, the precipitate was dried under vacuum. The percent yield and total amount of product was 22 kg (79% yield). NMR analysis showed that the product contained 98.6% of desired mPEG(20,000 Da)-BTC and 1.4% of starting mPEG(20,000 Da)-OH. No isopropyl benzotriazole carbonate was detected.

Comparative Example 8

Preparation of mPEG(20,000 Da)-BTC

Large Scale Synthesis with No Water Treatment

The large scale synthesis of mPEG(20,000 Da)-BTC described in the Example 7 was repeated but water was not added to the reaction mixture to hydrolyze residual di(1-benzotriazolyl)carbonate. NMR analysis showed that the final product contained 44 mol % of isopropyl benzotriazolyl carbonate. Thus, this experiment shows that large scale production with the need to isolate and remove activated carbonate reagents is possible. However, loss on precipitation is predicted to be 10-20% based on comparative experiments.

What is claimed is:
1. The composition resulting from carrying out the synthetic method comprising:
(a) combining a composition comprising an aprotic solvent and a hydroxy-terminated, water-soluble polymer having the following structure:

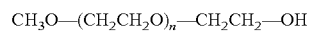

wherein (n) is an integer from 2 to about 4000, with a composition comprising di(1-benzotriazolyl) carbonate, wherein the composition comprising the di(1-benzotriazolyl) carbonate is added such that there is an excess of the di(1-benzotriazolyl) carbonate relative to the hydroxy-terminated, water-soluble polymer, to thereby result in a composition comprising an active carbonate ester of the water-soluble polymer having the following structure:

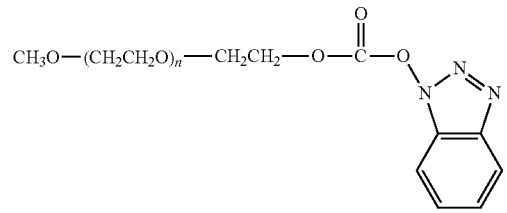

wherein (n) is an integer from 2 to about 4000, and unreacted di(1-benzotriazolyl) carbonate;
(b) adding a composition comprising a reactive molecule selected from the group consisting of water, a lower alkyl monohydric alcohol, hydrogen sulfide and a lower alkyl monobasic amine to the composition comprising the active carbonate ester of a water-soluble polymer and unreacted di(1-benzotriazolyl) carbonate, wherein the composition comprising the reactive compound is added such that substantially all of the unreacted di(1-benzotriazolyl) carbonate is substantially consumed;
(c) reacting the active carbonate ester of a water-soluble polymer lysine to form a polymeric lysine derivative;

(d) reacting the polymeric lysine derivative in one or more reactions to form a polymeric reagent; and (e) reacting the polymeric reagent with an active agent under conjugation conditions to thereby result in a water-soluble polymer-active agent conjugate.

2. The composition as in claim 1, wherein the reactive molecule is water.

3. The composition as in claim 1, wherein the reactive molecule is selected from hydroxyalkyl attached to a solid support, mercaptoalkyl attached to a solid support, primary amine attached to a solid support, and secondary amine attached to a secondary support.

4. The composition as in claim 1, wherein the polymeric lysine derivative has the following structure:

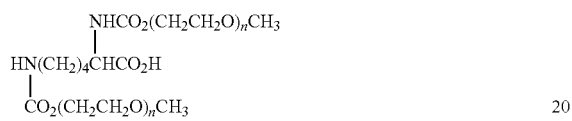

wherein each (n) is an integer from 2 to about 4000.

* * * * *